United States Patent [19]

Shaw

[11] 3,999,542
[45] Dec. 28, 1976

[54] ANTI-CLOGGING LIQUID ADMINISTRATION APPARATUS AND METHOD

[76] Inventor: Robert F. Shaw, 135 Willow Brook Drive, Portola Valley, Calif. 94025

[22] Filed: Apr. 10, 1975

[21] Appl. No.: 566,933

[52] U.S. Cl. .................. 128/214 R; 128/214 C; 128/214 E; 128/DIG. 12
[51] Int. Cl.² .................................. A61M 5/00
[58] Field of Search ....... 128/214 R, 214 A, 214 C, 128/214 E, 214 F, 214.2, DIG. 6, DIG. 12, DIG. 13

[56] References Cited
UNITED STATES PATENTS

| | | | |
|---|---|---|---|
| 3,242,924 | 3/1966 | Kraft et al. | 128/214 E |
| 3,884,228 | 5/1975 | Hahn | 128/DIG. 12 |
| 3,901,231 | 8/1975 | Olson | 128/214 F |

Primary Examiner—Louis G. Mancene
Assistant Examiner—Robert F. Cutting
Attorney, Agent, or Firm—A. C. Smith

[57] ABSTRACT

An improved method and means for preventing the intravascular needle of liquid infusion apparatus from clogging uses a delivery control means which operates in two modes at two liquid delivery rates. In the first operating mode, the delivery control means may be set to deliver liquid to a patient at a selected rate. In the second operating mode, the delivery control means supplies liquid at a slower rate which is sufficient to flush the needle. The transition from operation in the first mode to operation in the second mode is initiated in various ways in response to the volume of liquid delivered to a patient.

14 Claims, 3 Drawing Figures

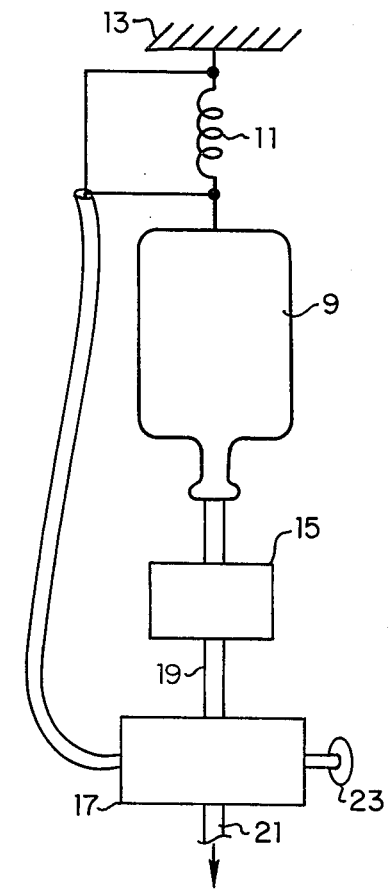
Figure 1
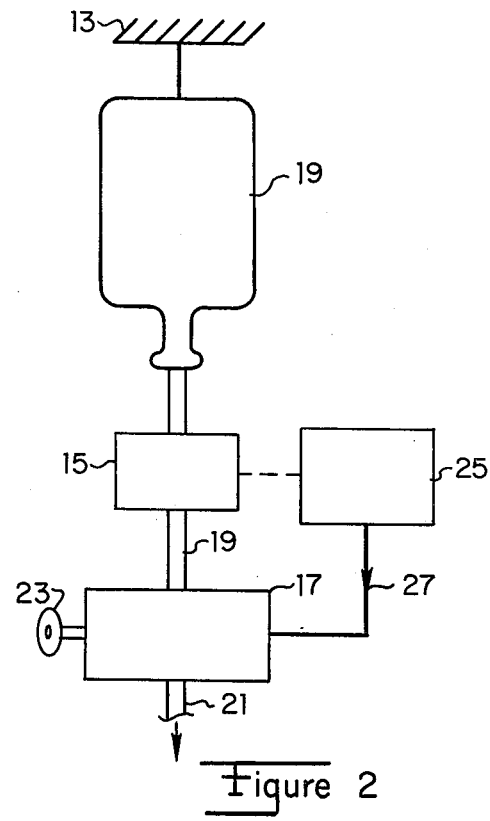
Figure 2
Figure 3
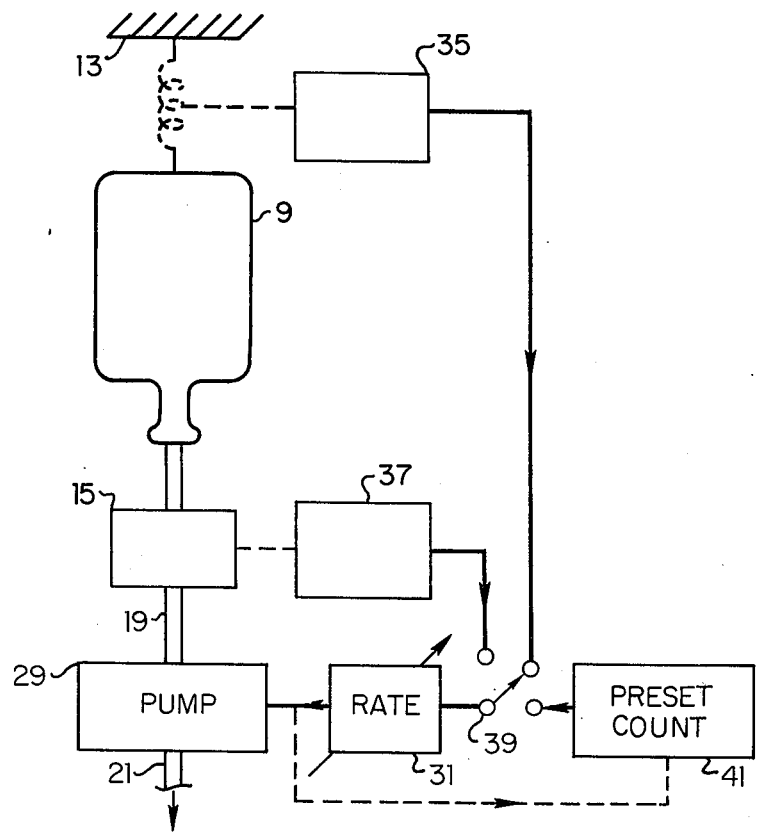

ANTI-CLOGGING LIQUID ADMINISTRATION APPARATUS AND METHOD

BACKGROUND OF THE INVENTION

Over eighty million intravenous infusions of substantial quantities of liquids containing various nutrients, minerals, drugs or blood are administered to patients each year in the United States. These intravenous (I.V.) infusions typically administer hundreds to thousands of cubic milliliters of liquid from glass or plastic reservoirs, through a conduit of plastic tubing which terminates in a hollow needle that pierces the skin and an underlying blood vessel, into which the liquid is administered.

It is believed that in approximately 15–20% of patients receiving I.V. infusions, blood clots form within the needle, clogging it and terminating the administration of the fluid, minerals, drugs or blood which are needed by the patient. A clogged needle must generally be replaced by an additional needle puncture at a new skin and blood vessel puncture site; though from time-to-time efforts are made to blow the blood clot out of the needle and into the patient's circulation by applying very high pressures to the clogged needle with a liquid-filled syringe. Such efforts, though undertaken to spare the patient the additional pain and tissue damage of added needle puncture, are generally regarded as less-than-optimal medical practice.

The offending clots within the needles that clog them and stop fluid administration consist of elements from the blood that flows in the region of the needle tip. These blood clots can form whenever the flow of fluid through the needle is interrupted for a sufficient period of time. This can occur whenever the supply of liquid within the reservoir is depleted or whenever cold flow of the plastic conduit or changes in the patient's position produce resistance within the conduit or at the needle tip with respect to the blood vessel wall that cannot be overcome by the hydrostatic head of pressure furnished by the practice of hanging the liquid reservoir above the patient.

To overcome such changes in resistance within the conduit and at the needle tip, positive displacement pumps are being employed with increasing frequency for administration of I.V. infusions. However, such pumps commonly introduce the danger that when the supply of liquid in the reservoir has been depleted, continued pumping can rapidly deplete the residual supply of liquid remaining in the conduit and cause air to be pumped into the patient with possible fatal results.

SUMMARY OF THE INVENTION

In accordance with the preferred embodiment of the present invention, a liquid-delivery control means responds to depletion of the supply of liquid within the reservoir by alerting attendant personnel and by converting to an operating mode in which the residual supply of liquid within the conduit is delivered to the patient at a much slower rate sufficient to prevent clots from forming in the needle for an extended period of time which provides attendant personnel opportunity to take corrective measures. This is accomplished by locating a liquid-delivery control means along the liquid conduit which extends from the reservoir to the needle for operation in two modes. In the first mode, the liquid delivery rate may be set to any desirable value; in the second mode, established in response to depletion of the residual supply of liquid in the reservoir, the supply of liquid within the conduit is delivered at a much slower rate which is sufficient to flush the needle and prevent clots from forming therein.

DESCRIPTION OF THE DRAWING

FIG. 1 is a pictorial view of one embodiment of the invention in which liquid delivery is controlled in response to the weight of liquid and reservoir and, hence, the volume of liquid in the liquid reservoir, operating in conjunction with a valve-type liquid delivery control means.

FIG. 2 is a pictorial view of another embodiment in which the liquid delivery is controlled by a valve that is responsive to the cessation of liquid being delivered from the reservoir; and FIG. 3 is a pictorial view of still another embodiment of the invention in which liquid delivery is controlled by positive displacement pumping of the liquid at rates which are determined by a selected parameter of the system.

DESCRIPTION OF THE PREFERRED EMBODIMENT

Referring now to FIG. 1, there is shown a reservoir of liquid which is supported by spring 11 from a support 13. A conventional dropforming chamber 15 may connect the outlet of the reservoir to the valve 17 via a length of tubing 19. The outlet of the valve 17 is coupled to an intravascular needle or catheter (not shown) by another length of tubing 21. The valve 17 may be mechanically coupled to the spring 11 by a length of control cable in order to operate the valve in one of two modes. In the first mode, responsive to the greater weight of a full reservoir 9, the valve 17 may be set by control knob 23 to any desired rate of liquid delivery. As the reservoir 9 empties and decreases its weight, the displacement of spring 11 also decreases. A conventional over-center or toggling mechanism may be actuated by the mechanical displacement of the spring 11 associated with a selected weight limit to operate in the second mode. In this mode, the remaining liquid in the drip chamber 15 and tubing 19 (and reservoir 9, if any) is delivered through the valve 17 at a much slower rate sufficient to flush the needle and prevent the formation of clots therein. At the same time that the valve 17 is changed over to the second mode, an alarm may be given either audible or visual, or the like, to alert attendant personnel to the conditions requiring replacement of the empty reservoir 9 with a full one. Of course, the mechanical coupling between the spring 11 and valve 17 may be selected to switch the valve over to operation in the second mode in response to only a portion of the liquid supply in reservoir 9 being delivered. The valve may alternatively operate by intermittently opening and closing rather than varying the size of the fluid flow path.

Referring now to FIG. 2, there is shown apparatus that is similar to the apparatus of FIG. 1, except that depletion of the supply of liquid in reservoir 8 is detected otherwise than by weight of the reservoir. Rather, a detector 25 is disposed to respond to liquid from the reservoir 9 forming drops in the drop forming chamber 15 to maintain the valve 17 operating in the first mode. The detector 25 may include a conventional photocell or other optical transducer which develops a signal on line 27 in response to recurring drops forming within the chamber 15. Of course, this detector 25 may also include an acoustic transducer which responds to the sound of recurring drops, or an impedance transducer, or the like, which operates to produce a signal on line 27 in response to recurring drops in chamber 15. The signal on line 27 may thus be used to maintain operation of the valve 17 in the first mode in which the flow rate may be selected by control knob 23.

However, when the supply of liquid in reservoir 9 is depleted and drops 25 no longer form in chamber 15, the detector no longer produces signal on line 27. In response thereto, an alarm may be given and the valve 17 switches over to operation in the second mode in which the residual supply of liquid in the drop chamber and conduit is delivered at a much slower rate, all as previously discussed in connection with the embodiment of FIG. 1.

Referring now to FIG. 3, there is shown another embodiment in which the liquid from reservoir 9 is delivered by positive displacement of pump 29 rather than by the static pressure head established by the position of the reservoir above the patient, as in FIGS. 1 and 2. Pump 29 may be an electrically-pulsed displacement pump, for example, of a type disclosed in U.S. Pat. No. 3,620,650 or 3,559,644 in which the liquid delivery rate is controlled by the pulse rate applied thereto by a signalcontrolled pulse generator 31. Of course, other pumps and controllers including ones driven by motors that are adjusted by speed control devices may also be used. In this embodiment, the pump rate controller (i.e., the pulse generator 31) may be coupled to respond to a weight transducer 35 that operates in response to the weight of the reservoir, or to a drop detector 37 that optically or acoustically or otherwise senses recurring drops for providing a control signal on line 39 to operate the pulse generator 31 in one of two modes. In the first mode, the pulse rate may be set to any desired value which, when applied to the pump 29, provides the desired liquid-delivery rate. However, when the supply of liquid (or a portion thereof) in reservoir 9 is depleted, or when the formation of drops stops, then the respective weight — or drop — detector 35, 37 no longer produces control signal on line 39. This causes pulse generator 31 which may include a conventional signal-controlled oscillator to operate in the second mode in which pulses are supplied to the pump 29 at a much slower rate to produce a much slower liquid delivery rate than in this prior mode for the same purposes previously discussed in connection with the embodiments illustrated in FIGS. 1 and 2.

Alternatively, a preset counter 41 may be included to provide the control signal on line 39. This counter may be connected to count the total number of pulses supplied by the generator 31 to the pump 29 as an accumulating indication of the volume of liquid pumped thereby. When the accumulated total equals the preset count (thereby indicating a selected volume has been pumped equal to the total volume of the reservoir or a portion of that volume, as desired), the pulse generator may be switched to the second mode of operation for operating the pump 29 at a much slower liquid delivery rate as previously described.

I claim:

1. The method of infusing liquid from a reservoir into a patient through a liquid-delivery conduit including an intravascular conduit which is inserted into a patient, the method comprising the steps of:

infusing liquid from the reservoir into the patient at a first selected delivery rate;
 detecting the infusion of a selected volume of liquid into the patient; and
 thereafter infusing liquid into the patient at a second delivery rate which is slower than the first delivery rate and which is sufficient to flush the intravascular conduit to prevent clogging by the formation of blood clots therein.

2. The method of infusing liquid into a patient according to claim 1, wherein in the step of detecting depletion of substantially the supply of liquid in the reservoir is detected; and
 in the step of infusing liquid thereafter, the liquid in residual supply is infused into this patient at said slower rate.

3. The method of infusing liquid into a patient according to claim 1 wherein in the step of detecting, the weight of the reservoir and liquid therein is detected as an indication of said selected volume of liquid; and
 in the step of infusing liquid thereafter, liquid is delivered at said second delivery rate in response to the weight of the reservoir and liquid therein attaining a selected value.

4. The method of infusing liquid into a patient according to claim 1 wherein said liquid delivery conduit includes a drop forming chamber; and
 in the step of detecting, the occurrences of liquid drop formation are detected as an indication of said selector volume of liquid
 in the step of infusing liquid thereafter, liquid is delivered at said second delivery rate in response to the number of drop formation occurrences attaining a selected value.

5. The method of infusing liquid into a patient according to claim 1 wherein said liquid delivery conduit includes a drop forming chamber; and
 in the step of detecting, the occurrence of liquid drop formation is detected as an indication of said selector volume of liquid
 in the step of infusing liquid thereafter liquid is delivered at said second delivery rate in response to the absence of drop formation.

6. The method of infusing liquid into a patient according to claim 1 wherein the step of infusing liquid is performed by positive displacement pumping.

7. The method of infusing liquid into a patient according to claim 6 wherein in the step of detecting, the product of stroke volume times stroke rate is detected as an indication of volume of infused liquid; and
 in the step of infusing liquid thereafter, liquid is delivered at said second delivery rate in response to the product of stroke volume and stroke rate attaining a selected value.

8. Apparatus for infusing liquid from a reservoir into a patient through a liquid delivery conduit including an intravascular conduit which is inserted into a patient, the apparatus comprising:
 liquid-delivery control means communicating with the liquid-delivery conduit at a location therealong intermediate the reservoir and needle, said liquid-delivery control means being operable in a first mode in which liquid is delivered thereby at a selected rate and in a second mode in which liquid is delivered thereby at a rate slower than said selected rate during operation in the first mode and sufficient to flush the intravascular conduit to prevent clogging by formation of blood clots therein; and detector means coupled to said liquid-delivery control means for converting the operation thereof from the first mode to the second mode in response to detection of a condition which is representative of the volume of liquid delivered.

9. Apparatus as in claim 8 wherein said detector means includes a weight sensor for producing said conversion in operation of said liquid-delivery control means in response to the weight of said reservoir and its contents attaining a selected value.

10. Apparatus as in claim 8 wherein said conduit includes a drop-forming chamber and said detector means includes a drop detector disposed with respect to said drop-forming chamber for producing the conversion in operation of said liquid-delivery control means in response to the absence of drop formation in drop-forming chamber.

11. Apparatus as in claim 8 wherein said conduit includes a drop-forming chamber and said detector means includes a drop detector disposed with respect to said drop-forming chamber for producing the conversion in operation of said liquid-delivery control means in response to the total number of drops formed attain a selected value.

12. Apparatus as in claim 8 wherein said liquid-delivery control means includes valving apparatus for introducing variations in obstruction to fluid flow through the liquid delivery conduit.

13. Apparatus as in claim 8 wherein said liquid delivery control means includes positive displacement pumping apparatus.

14. Apparatus as in claim 13 wherein said detector means responds to the product of stroke volume times stroke rate of said pumping apparatus attaining a selected value to convert operation of said liquid-delivery control means from said first mode to said second mode.

* * * * *